US 9,262,827 B2

(12) United States Patent
Brown et al.

(10) Patent No.: US 9,262,827 B2
(45) Date of Patent: Feb. 16, 2016

(54) LUNG, LOBE, AND FISSURE IMAGING SYSTEMS AND METHODS

(71) Applicant: THE REGENTS OF THE UNIVERSITY OF CALIFORNIA, Oakland, CA (US)

(72) Inventors: Matthew S. Brown, Marina del Ray, CA (US); Pechin Lo, Los Angeles, CA (US); Eva Marjolein Van Rikxoort, Lent (NL); Jonathan Gerald Goldin, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/643,935

(22) Filed: Mar. 10, 2015

(65) Prior Publication Data

US 2015/0254843 A1    Sep. 10, 2015

Related U.S. Application Data

(63) Continuation of application No. PCT/US2013/057753, filed on Aug. 31, 2013.

(60) Provisional application No. 61/700,829, filed on Sep. 13, 2012.

(51) Int. Cl.
*G06K 9/00* (2006.01)
*G06T 7/00* (2006.01)
(Continued)

(52) U.S. Cl.
CPC ............. *G06T 7/0012* (2013.01); *G06T 7/0038* (2013.01); *G06T 7/0081* (2013.01); *G06T 7/0083* (2013.01); *G06T 7/602* (2013.01);
*G06T 7/608* (2013.01); *G06T 15/08* (2013.01); *A61B 6/032* (2013.01); *G06T 2200/04* (2013.01); *G06T 2207/10081* (2013.01); *G06T 2207/20044* (2013.01); *G06T 2207/20076* (2013.01); *G06T 2207/20101* (2013.01);
(Continued)

(58) Field of Classification Search
None
See application file for complete search history.

(56) References Cited

U.S. PATENT DOCUMENTS 8,526,697 B2 * 9/2013 Blaffert et al. ........ G06T 7/0081
382/131
8,611,623 B2 * 12/2013 Kurihara et al. ...... G06T 7/0085
382/128
(Continued)

FOREIGN PATENT DOCUMENTS

JP    2006-517822 A    8/2006

OTHER PUBLICATIONS

Brown, et al., "Knowledge-based segmentation of thoracic computed tomography images for assessment of split lung function, Medical Physics," vol. 27, No. 3, Mar. 2000, pp. 592-598.*
(Continued)

*Primary Examiner* — Shefali Goradia
(74) *Attorney, Agent, or Firm* — John P. O'Banion

(57) ABSTRACT

An automated or semi-automated system and methods are disclosed that provide a rapid and repeatable method for identifying lung, lobe, and fissure voxels in CT images, and allowing for quantitative lung assessment and fissure integrity analysis. An automated or semi-automated segmentation and editing system and methods are also disclosed for lung segmentation and identification of lung fissures.

28 Claims, 9 Drawing Sheets

(51) Int. Cl.
  *G06T 7/60* (2006.01)
  *G06T 15/08* (2011.01)
  *A61B 6/03* (2006.01)

(52) U.S. Cl.
  CPC ............... *G06T 2207/20116* (2013.01); *G06T 2207/20136* (2013.01); *G06T 2207/20141* (2013.01); *G06T 2207/20148* (2013.01); *G06T 2207/20156* (2013.01); *G06T 2207/30061* (2013.01)

(56) References Cited

U.S. PATENT DOCUMENTS

| | | | |
|---|---|---|---|
| 2007/0058870 A1 | 3/2007 | Liang et al. | |
| 2007/0092864 A1* | 4/2007 | Reinhardt et al. | A61B 19/52 435/4 |
| 2007/0103464 A1 | 5/2007 | Kaufman et al. | |
| 2007/0165917 A1 | 7/2007 | Cao et al. | |
| 2009/0185731 A1* | 7/2009 | Ray et al. | G06T 7/0012 382/131 |
| 2010/0322493 A1 | 12/2010 | Wei et al. | |
| 2014/0298270 A1* | 10/2014 | Wiemker; Rafael | A61B 6/466 715/849 |

OTHER PUBLICATIONS

Korean Intellectual Property Office (KIPO), International Search Report and Written Opinion, PCT/US2013/057753, issued Dec. 23, 2013, pp. 1-10, with claims searched, pp. 11-16, corresponding to U.S. Appl. No. 14/643,935.

Eva M van Rikxoort et al., "Automated segmentation of pulmonary structures in thoracic computed tomography scans: a review", Phys. Med. Biol. 58 (2013) R187-R220, published Aug. 16, 2013.

* cited by examiner

LUNG, LOBE, AND FISSURE IMAGING SYSTEMS AND METHODS

CROSS-REFERENCE TO RELATED APPLICATIONS

This application is a 35 U.S.C. §111(a) continuation of PCT international application number PCT/US2013/057753 filed on Aug. 31, 2013, incorporated herein by reference in its entirety, which claims priority to, and the benefit of, U.S. provisional patent application Ser. No. 61/700,829 filed on Sep. 13, 2012, incorporated herein by reference in its entirety. Priority is claimed to each of the foregoing applications.

The above-referenced PCT international application was published as PCT International Publication No. WO 2014/042902 on Mar. 20, 2014, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to computed tomography imaging, and more particularly to computed tomography imaging incorporating lung, lobe and fissure image segmentation and analysis.

2. Description of Related Art

Computed Tomography (CT) imaging has been used for in vivo assessment of the location, extent, and progression of lung disease in patients. However, the role of diagnostic imaging has generally been limited to visual inspection in clinical practice. In order to enable quantitative analyses in clinical trials and practice, computer-aided methods are important to perform these analyses routinely and reliably in large patient cohorts.

For analysis to be feasible in clinical practice, reliable automation is needed based on the size of the data sets (>400 cross-sectional images for isotropic voxel spacing). Extraction of the lung fields on CT images is relatively straightforward because of the high contrast with surrounding soft-tissue structures. However, subdivision (segmentation) of the lungs into lobes is much more challenging because they are separated by only a thin layer of tissue (fissure). These fissures are very faint due to partial volume averaging.

Current lung segmentation methods are typically based on attenuation thresholding and region-growing to identify the lung fields from the surrounding tissue. Automated lobar segmentation is much more difficult and a small number of research groups are currently working on this problem. Approaches are typically threshold or edge-based and use some information regarding continuity in the longitudinal direction. Most use limited domain knowledge applied in the form of heuristics in the segmentation algorithm, although we are beginning to see more powerful atlas-matching approaches being developed.

Current approaches have not as yet yielded a robust automated lobar segmentation that is reliable enough to be used routinely in clinical practice. These challenges arise because partial volume averaging of the thin fissural plane leads to very faint, incomplete edges that indicate the lobar boundary. Also, in many patients the fissures are anatomically incomplete (i.e., they do not extend all the way across the lung parenchyma). Anatomic and pathological variants in shape and location of fissures also create problems, particularly when disease such as emphysema is present, as this leads to severe deformities. CT technical factors can also change the fissure appearance and image characteristics. The minor fissure of the right lung is particularly difficult to identify because it tends to run parallel to the scan plane and is more variable in shape.

Accordingly, an object of the present invention is an automated or semi-automated system that provides a rapid and reliable method for identifying lung, lobe, and fissure voxels in CT images, so that quantitative lung assessment can be performed in clinical practice. Another object is a system that provides fissure integrity analysis. A further object is a semi-automated segmentation and editing system for lung segmentation and identification of the fissures that are robust across large patient cohorts.

At least some of the above objectives will be met in the following description.

BRIEF SUMMARY OF THE INVENTION

The present invention incorporates automated and interactive systems for lung image analysis, in particular the integration of a user-interactive fissure surface deformation method.

In one aspect of the invention, a method is disclosed for segmentation of the lung fields in CT images incorporating threshold-based region-growing and morphology for segmentation followed by fuzzy logic to match image regions to anatomical structures. In one embodiment, image segmentation is performed using a combination of gray-level thresholding, three-dimensional (3-D) region-growing and maximum cost paths. Data from an anatomical model may also be used to spatially constrain the algorithms of the present invention.

In another aspect of the invention, a maximum cost path algorithm is used to segment anterior and posterior junction lines of lung CT image data.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Figure 1:
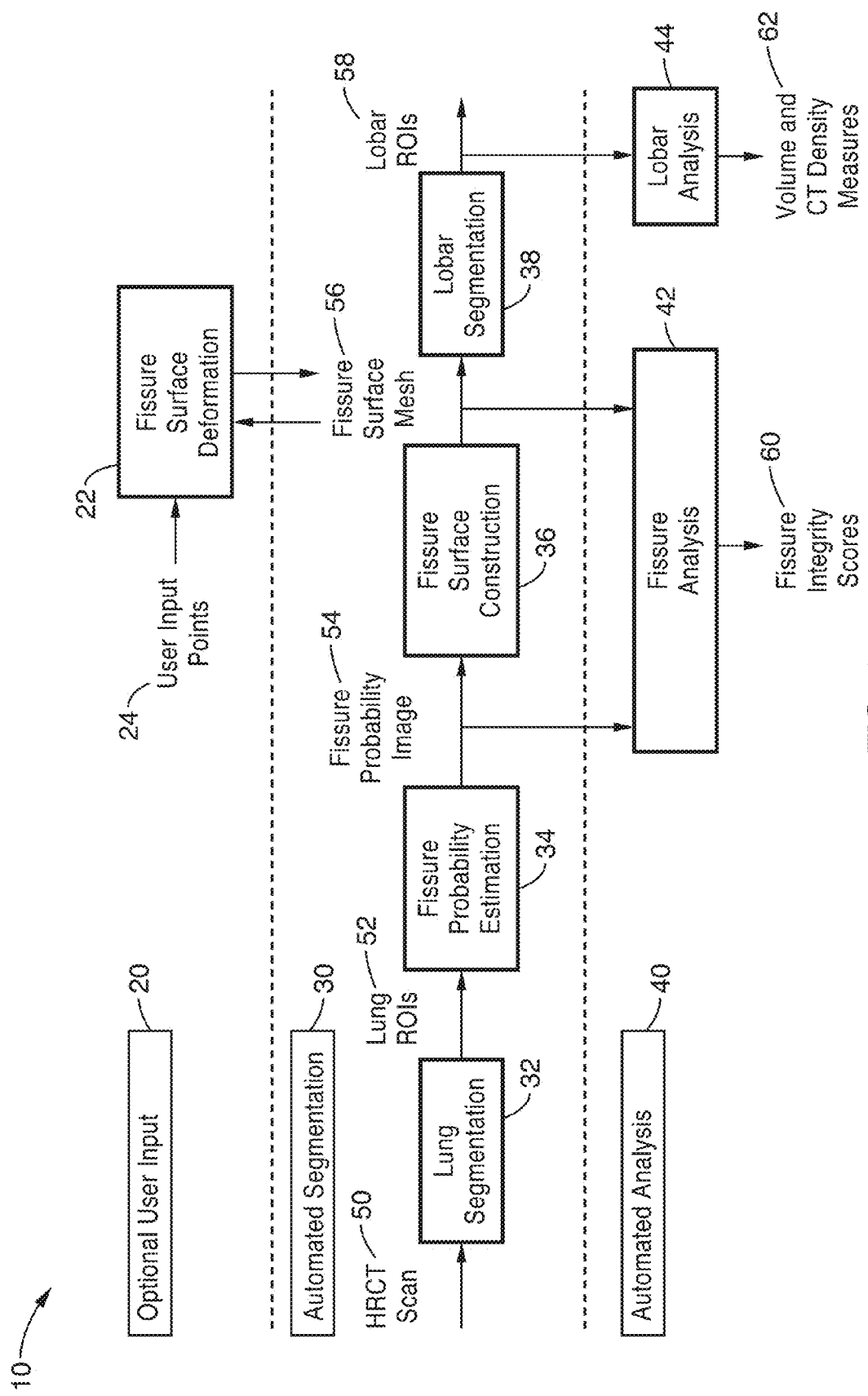
FIG. 1 is an overview flow diagram of the lung, lobe and fissure image segmentation method of the present invention.

FIG. 1 illustrates an overview flow diagram of the lung, lobe and fissure image segmentation method 10 of the present invention. Method 10 includes an automated segmentation module 30 which may receive input from user input module 20. Data output from the automated segmentation module 30 may be used in an automated analysis module 40 for fissure and lobar analysis of the automated segmentation. Each of the steps in lung segmentation model 30 are shown in greater detail in FIG. 2 through FIG. 6.

The automated segmentation module 30 takes high resolution computed tomography (HRCT) scan data as input and for lung segmentation step 32, which generates lung ROI data 52. The ROI data 52 is used in fissure probability estimation step 34 to generate fissure probability image 54, which is then used in fissure surface construction step 36 to create fissure surface mesh 56. Data from the fissure probability image 54 and fissure surface mesh 56 may be output to fissure analysis step 42 to generate fissure integrity scores 60. Additionally, user input points 24 may be applied to the output fissure surface mesh 56 via fissure surface deformation step 22. Fissure surface mesh 56 is used in lobar segmentation step 38 to generate lobar ROI's 58, which may be further analyzed via lobar analysis step 44 to create volume and CT density measurements 62.

Segmentation of the lung fields in CT images incorporates threshold-based region-growing and morphology for segmentation followed by fuzzy logic to match image regions to anatomical structures. The system and methods of the present invention include enhancements to fill holes and improved central airway segmentation. Image segmentation is performed using a combination of gray-level thresholding, three-dimensional (3-D) region-growing and maximum cost paths. The algorithms are spatially constrained using information from the anatomical model.

Due to CT volume averaging effects, the anterior and sometimes posterior junctions between the right and left lungs may have relatively low CT numbers. Therefore, thresholding may not separate the individual lung fields, i.e. they may be extracted as a single contiguous set of voxels, falsely joined at the junction line. Therefore a maximum cost path algorithm is used to segment the anterior and posterior junction lines. The cost of each pixel is proportional to the CT number, and since the pixels that form the junction have a slightly higher CT number than the surrounding lung, the maximum cost path should identify them.

Figures 2, 3:
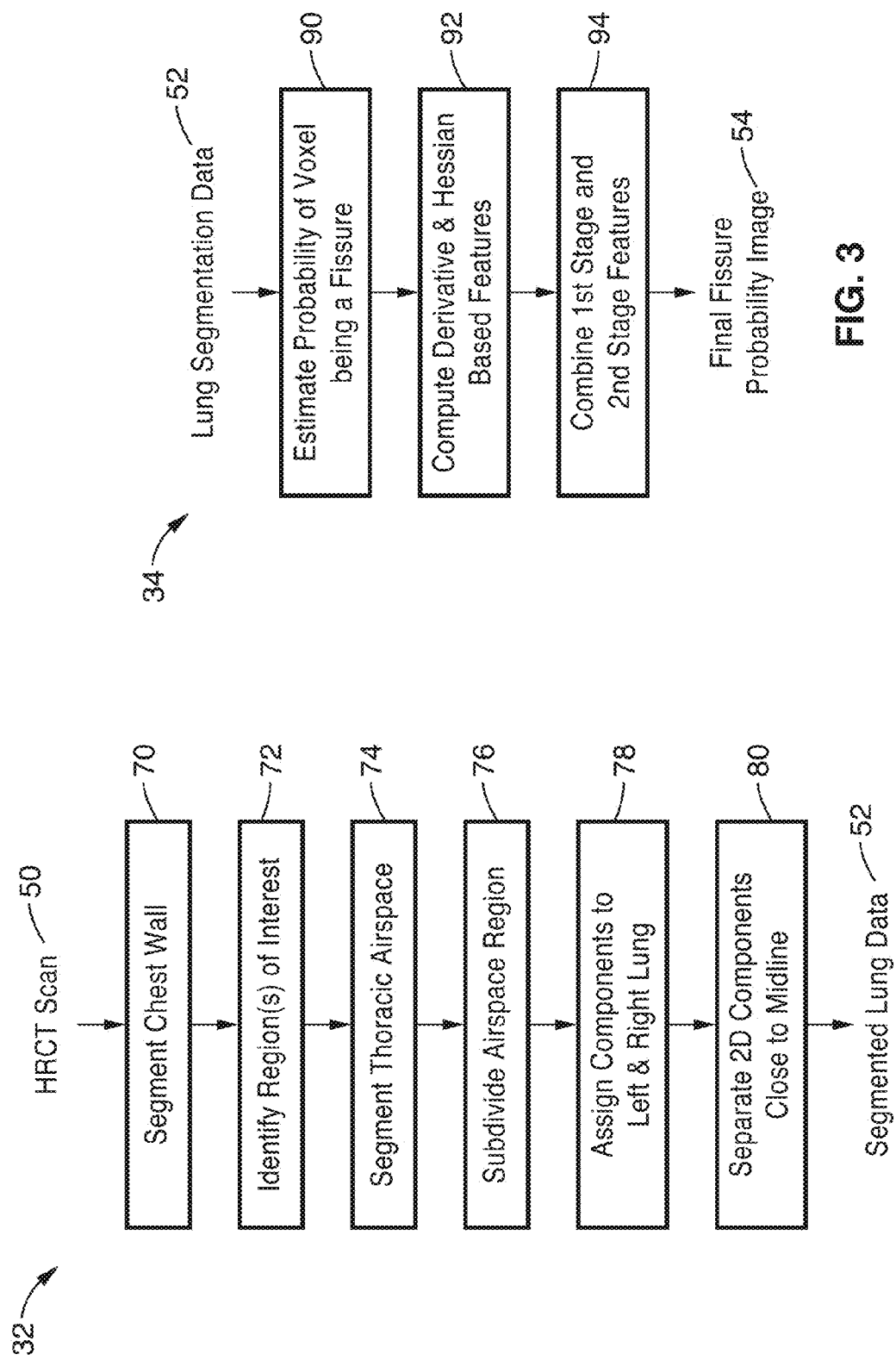
FIG. 2 is a detailed flow diagram of the lung segmentation step of FIG. 1.
FIG. 3 is a detailed flow diagram of the fissure probability estimation step of FIG. 1.

FIG. 2 shows a detailed flow diagram of the lung segmentation step 32. Using the HRCT scan data 50 (see also FIG. 1), the chest wall is first segmented at step 70 by intensity-thresholding bright voxels and selecting the largest 3D connected component. Next, at step 72, an ROI comprising voxels inside the chest wall are identified to constrain further segmentation of the lungs. At step 74, the thoracic airspace is segmented by intensity-thresholding dark voxels and selecting the largest 3D connected component. The airspace region is then subdivided into axial 2D connected components at step 76. At step 78, 2D components having a centroid right of the midline are assigned to the right lung, and components to the left are assigned to the left lung. Finally, at step 80, 2D components with a centroid close to the midline are separated by detecting the maximum intensity cost path in the region of the midline, and the separated components are assigned to the right and left lungs to generate the segmented lung data 52.

FIG. 3 is a detailed flow diagram of the fissure probability estimation step 34. A 2-stage supervised fissure enhancement filter is applied to the CT scan to generate a fissure probability image 54. A set of Gaussian derivative and Hessian based features are computed at different scales for each lung voxel identified in the CT scan 50. The features are input to a binary K-nearest-neighbor (KNN) classifier with exemplars comprising fissures and non-fissures. The result is a 1st-stage image at step 90 that estimates the probability of a voxel being a fissure as the number of nearest-neighbor exemplars that are fissures divided by k.

At 2nd-stage step 92, Gaussian derivative and Hessian based features are computed from the 1st-stage probability image of step 90. Features derived during the 1st-stage and 2nd-stage are then combined and input to a 2nd-stage KNN classifier at step 94 to obtain a final fissure probability 54.

Figure 4:
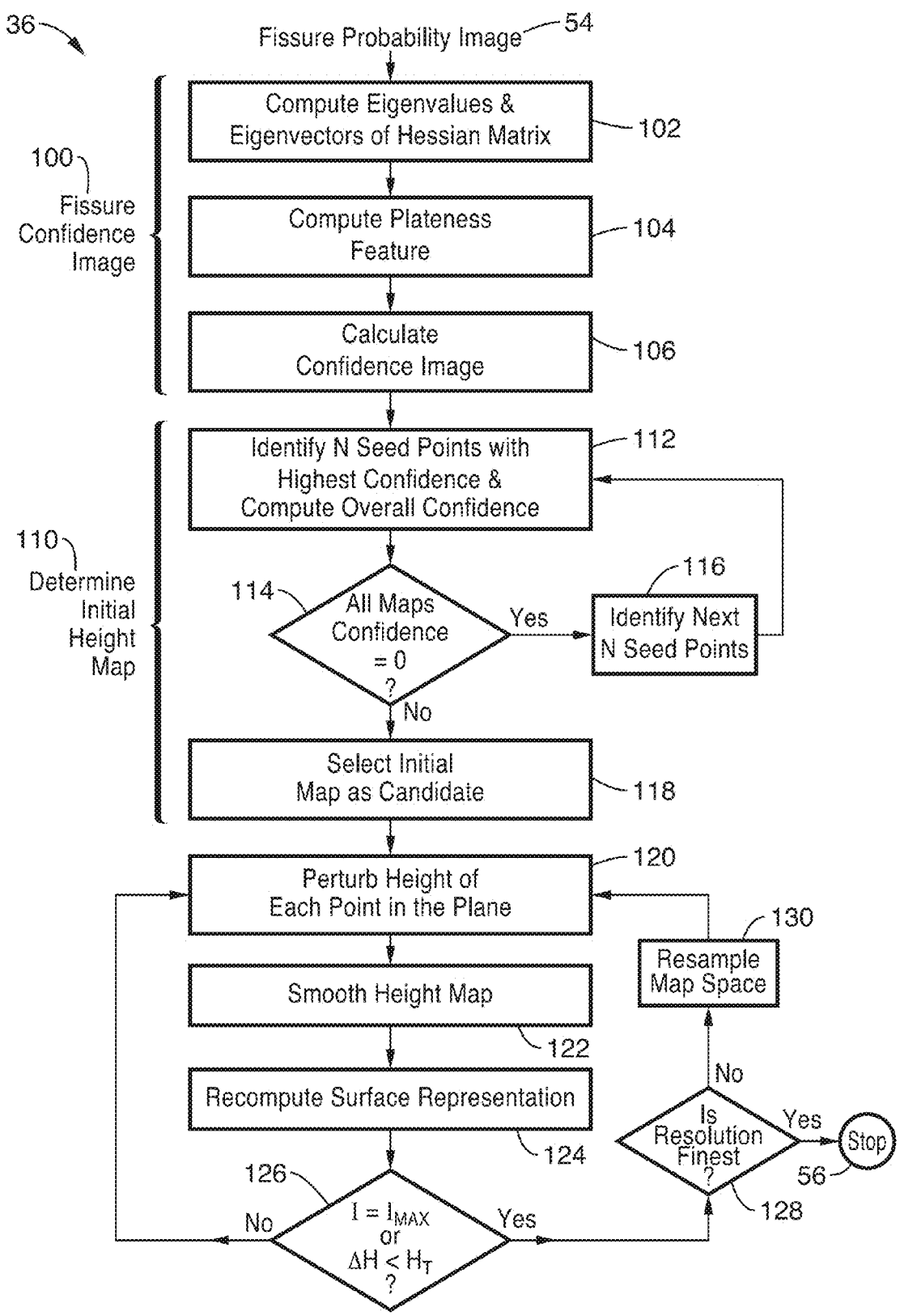
FIG. 4 is a detailed flow diagram of the fissure surface construction step of FIG. 1.

FIG. 4 shows a detailed flow diagram of the fissure surface construction step 36. To construct a surface mesh based on a given point cloud, the 3D surface is represented as a height map from a 2D reference plane. Given a set of surface points $P=\{p_1, p_2, \ldots, p_N\}$, where $p_i \in \mathbb{R}^3$, a 2D plane is constructed that best fits P in terms of mean square error. Such a plane will pass through the centroid $\bar{p}$ of P and have a normal n given by the normalized eigenvector of the largest eigenvalue of the covariance matrix C, which is defined in Eq. 1:

$$C = \frac{1}{N} \sum_{i=1}^{N} (p_i - \bar{p}) \cdot (p_i - \bar{p})^T \qquad \text{Eq. 1}$$

The surface can then be re-parameterized into a height map for a more compact representation, where the magnitude at a particular point $x \in \mathbb{R}^2$ on the reference plane reflects the height or displacement in the direction of n of that point on the 3D surface.

To generate a surface mesh from the fissure probability image 54 from step 34, a fissure confidence image 100 is computed at step 102 by first calculating eigenvalues and eigenvectors of the Hessian matrix, for each voxel x in the probability image 54.

Next, a plateness feature, plateness(x), is computed at step 104 for each voxel according to Eq. 2:

$$plateness(x) = 1 - \left|\frac{\lambda_2(x)}{\lambda_3(x)}\right|, \qquad \text{Eq. 2}$$

where $\lambda_2(x)$ and $\lambda_3(x)$ are the second largest and the largest eigenvalue of the voxel.

Based on the probability and plateness, a confidence image is then derived at step 106, where the confidence for each voxel, confidence(x), is calculated according to Eq. 3:

$$confidence(x) = \begin{cases} plateness(x) + probability(x), & \text{for } \lambda_3(x) < 0 \\ 0, & \text{otherwise} \end{cases} \qquad \text{Eq. 3}$$

At the lowest resolution level of the confidence image 100, an initial height map 110 is generated by deriving candidate maps from seed points and then selecting the best. At step 112, N seed points 50 with highest confidence are identified (and removed from further selection as seeds) to compute the overall confidence.

Figures 5, 6:
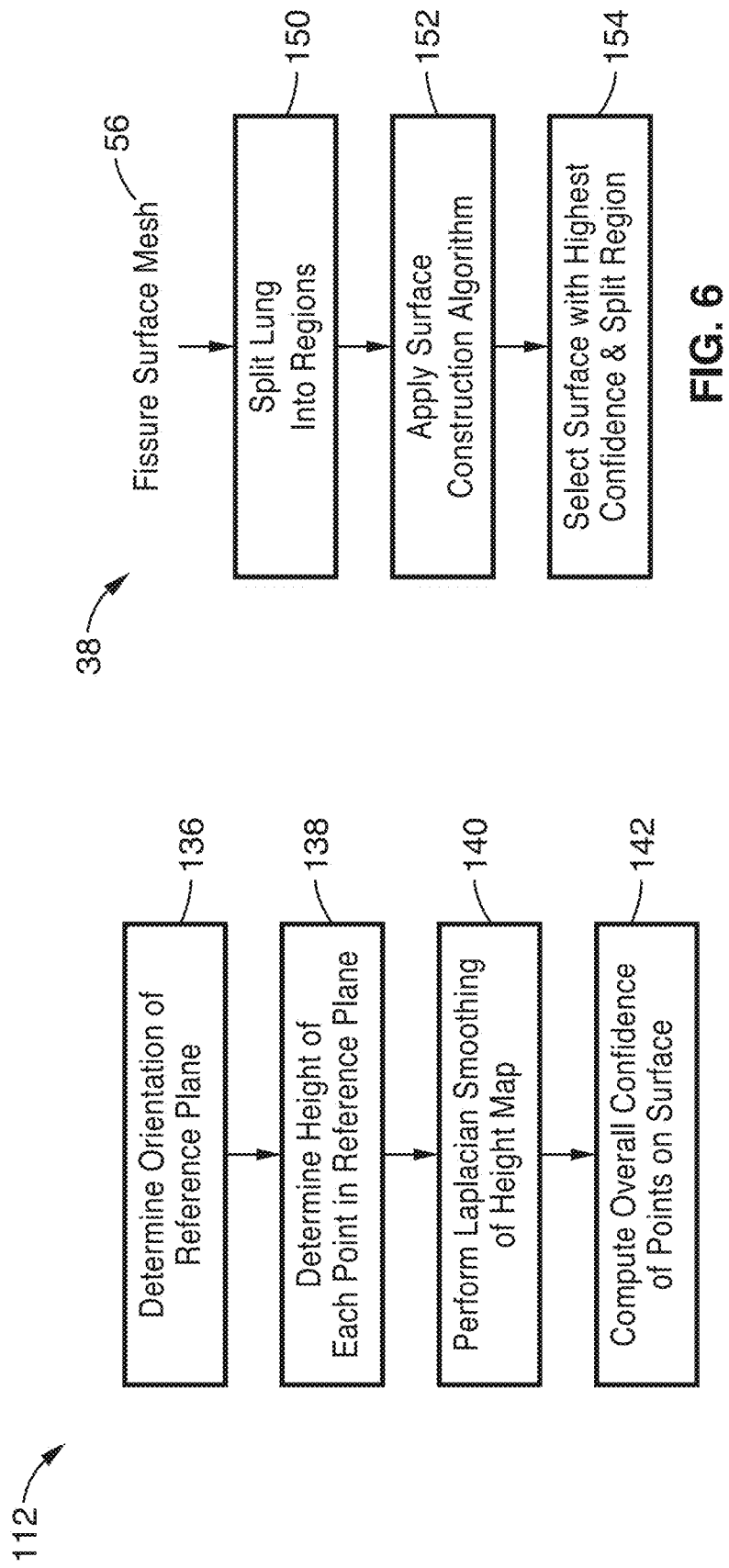
FIG. 5 is a detailed flow diagram of the seed point identification step of FIG. 4
FIG. 6 is a detailed flow diagram of the lobar segmentation step of FIG. 1.

Referring to FIG. 5, which illustrates step 112 in further detail, for each seed point, the Hessian eigenvectors of the seed point are used to determine the orientation of a reference plane at step 136. At step 138, the height of each point on the reference plane is determined based on the confidence image 100 by searching along the projection (normal to the reference plane) to find the point with locally maximum confidence. The search for the local confidence maximum is constrained for a given point based on the heights of its neighbors. At step 140, Laplacian smoothing is then performed on the height map. Finally, at step 142, the overall (median) confidence of points on the surface represented by the map is computed.

Referring back to FIG. 4, if all maps have an overall confidence of zero at step 114, then step 112 is repeated with the next N (e.g. 50) seed points 116 to generate up to a maximum of 100 candidate maps from seed points. If not, the initial map is selected as the candidate with the best overall confidence at step 118. If the overall confidence of all of the maps are zero, the selection is repeated using a secondary score, defined as the ratio of the number of non-zero confidence points and the total number of points (within the lung mask) in the reference plane.

At step 120, the height of each point on the reference plane is perturbed to a local confidence maximum within a local region of the height in the previous iteration. Next the height map is smoothed in step 122, and the surface representation (2D reference plane and height map) is re-computed (without height perturbation) in step 124.

At step 126, if the max iteration number is reached ($I = I_{max}$), or the maximum change in the height of the map $\Delta H$ is lower than a minimum threshold value $H_T$, then the algorithm continues to step 128. Otherwise, steps 120 to 124 are repeated. At step 128, if the map is not at the finest resolution, then the map space is resampled at a finer resolution at step 130 and steps 120 to 124 repeated. If finest resolution is reached at step 128, the iteration stops at step 56.

FIG. 6 is a detailed flow diagram of the lobar segmentation step 38 of FIG. 1 for the right lung. The right lung is assumed to have two fissures, and thus the lung is divided into two regions at step 150 (similar to the left lung). The surface construction algorithm 36 is then applied to each of the two regions in step 152. Next, the surface with the highest overall confidence score is selected, and its corresponding region is split into two at step 154. The result is that three lobar regions 58 (right upper, middle, and lower lobes) are obtained.

The left lung is assumed to have a single fissure, so the fissure probability estimation algorithm 34 and surface construction algorithm 36 are applied within the left lung region (from segmentation step 32) to generate the surface representing this fissure, and the lung is accordingly split into two regions (left upper and left lower lobe).

The segmented lobe regions 58 may also be used to derive labeled fissures. For example, the left major fissure is assigned to voxels belonging to the left upper lobe that are neighboring to a voxel belonging to the left lower lobe. The right major fissure is assigned to voxels belonging to the lower lobe that are neighboring to a voxel that belongs to either the upper or middle lobe. The right minor fissure is assigned to voxels belonging to the upper lobe that are neighboring to a voxel that belongs to the middle lobe.

Referring back to FIG. 1, the computed fissure surfaces 56 can be interactively modified by a human user (e.g. user deformation of fissure surfaces) for recomputing the lung lobes. The fissure surfaces 56 are first re-sampled into a height map (as shown in FIG. 4), where each point is at least 5 units (in the reference plane) away from the other surface points, resulting in an initial mesh $P_0$. A set of new user inputted points from a graphical user interface (GUI) are defined as $P_u$.

To update the surface, a radius of influence, r, is computed for each point $p_i \in P_u$ by applying the following algorithm with $P = P_u$. Instead of fixing the value of r, r is estimated from the points in P with projected coordinates near to those of $p_i$, by taking a subset of points $P_s(p_i) \subset P$ centered around $p_i$, which is sampled such that the points in $P_s(p_i)$ are at least 10 units away from each other on the reference plane. The resulting $r_i$ for $p_i$ is defined according to Eq. 4 and Eq. 5:

$$r_i = \min(\max(\min_{p \in P_s(p_i) \text{ and } p \neq p_i} r(p; p_i), r_{min}), r_{max}), \text{ where} \qquad \text{Eq. 4}$$

$$r(p; p_i) = \begin{cases} \infty, & \text{if } h_p(p) > h_p(p_i) \\ \dfrac{\pi \|t(p) - t(p_i)\|_2}{\mathrm{acos}\left(\dfrac{2h_p(p)}{h_p(p_i)} - 1\right)}, & \text{if } h_p(p)h_p(p_i) \geq 0 \\ \|t(p) - t(p_i)\|_2 \left(\dfrac{|h_p(p_i)|}{|h_p(p)| + |h_p(p_i)|}\right), & \text{otherwise} \end{cases} \qquad \text{Eq. 5}$$

otherwise where $\|\cdot\|_2$ is the Euclidean norm, $t(\cdot)$ is a function that projects a point in P to its corresponding coordinate on the reference plane, $h_p(\cdot)$ is a function that gives the height of a point in P on the map, r is the radius of the influence function, and $r_{min}$ and $r_{max}$ are the allowed minimum and maximum radius, which are set to 25 and 50 respectively. Any points in $P_0$ that fall under the influence of a new user input point, $P_u$, are removed from $P_0$. The radius of each point $p_i \in P_0$ is then computed, with $P = P_0 \cup P_u$.

For each point $p_i \in P$, the cosine-based influence function according to Eq. 6 is used to determine the influence that the point $p_i$ has on a neighboring point x:

$$w(x; p_i) = \begin{cases} \frac{1}{2}\left(\cos\left(\frac{\pi}{r}\|x - t(p_i)\|_2\right) + 1\right), & \text{if } \|x - t(p_i)\|_2 \leq r \\ 0, & \text{otherwise} \end{cases} \quad \text{Eq. 6}$$

The influenced height at x is then computed as $w(x; p_i)h_p(p_i)$.

For points on the reference plane that do not have a corresponding point in P (i.e. $x \neq t(p_i) \forall p_i \in P$), the overall influence from P for a point x in the 2D map is defined according to Eq. 7 and Eq. 8:

$$h_c(x) = w(x; p_s)h_p(p_s), \text{ with} \quad \text{Eq. 7}$$

$$p_s = \underset{p_i \in P}{\operatorname{argmax}} |w(x; p_i)h_p(p_i)| \quad \text{Eq. 8}$$

A characteristic of the cosine based influence function (Eq. 6) is that its influence is relatively local to the points in $P = P_0 \cup P_u$, especially with the proposed dynamically estimated $r_i$. To overcome this, an additional influenced height $h_1(x)$, which is based on the linear interpolation of the heights from all the points in P, is used. The computation of this linearly interpolated height for x is based on a linear tensioning algorithm. The final height for a point x in the height map is computed according to Eq. 9:

$$h_{map}(x) = \begin{cases} h_p(p_i), & \text{if } x = t(p_i) \text{ and } p_i \in P \\ \max(h_c(x), h_1(x)), & \text{otherwise} \end{cases} \quad \text{Eq. 9}$$

The final height map is preferably smoothed using the HO-algorithm instead of a Laplacian smoothing algorithm. The main advantage of that HO-algorithm has over the Laplacian smoothing algorithm is that it does not have the deformation and shrinkage problem of the latter.

After updating of the labeled fissure surfaces, the left major fissure is used to subdivide the left lung region into upper and lower lobe regions. The right major fissure is used to subdivide the right lung region into two regions, the bottom region is the right lower lobe and the top region is further subdivided in the right upper and middle lobes using the right minor fissure.

As shown in FIG. 1, an automated analysis module 40 may include quantitative assessment including lobar analysis step 44 to generate lung and lobar volume and density measurements 62, and fissure analysis step 42 to generate fissure integrity scores 60.

The segmentation steps 34 yield sets of voxels representing each lung and each lobe. To compute the volume of a given lung or lobe, the volumes of each of the included voxels are summed. Lung density statistics 62 may be computed over the Hounsfield Unit values of each voxel.

The fissure integrity 60 may also be computed for each lobe using fissure analysis 42. The left lower lobe fissure integrity is computed by classifying each voxel identified as a left major fissure (from lobar data 58) as "fissure present" if there is a fissure enhanced voxel with probability above a threshold within a local neighborhood. The percentage completeness is computed as the number of "fissure present" voxels over the total number of voxels. The left upper lobe fissure integrity is equal to the left lower lobe integrity. The right lower lobe fissure integrity is computed similarly using the voxels identified as the right major fissure (from lobar data 58).

The right middle lobe fissure integrity is computed over the set of voxels belonging to the right middle lobe that are neighboring to a voxel that belongs to either the upper or lower lobe. Each voxel identified as a right middle lobe fissure (from lobar data 58) is then classified as "fissure present" if there is a fissure enhanced voxel with probability above a threshold within a local neighborhood. The percentage completeness is computed as the number of "fissure present" voxels over the total number of voxels.

The right upper lobe fissure integrity is computed by calculating the set of voxels belonging to the right upper lobe that are neighboring to a voxel that belongs to either the middle or lower lobe. Each voxel identified as a right upper lobe fissure (from lobar data 58) is then classified as "fissure present" if there is a fissure enhanced voxel with probability above a threshold within a local neighborhood. The percentage completeness is computed as the number of "fissure present" voxels over the total number of voxels.

Figure 8:
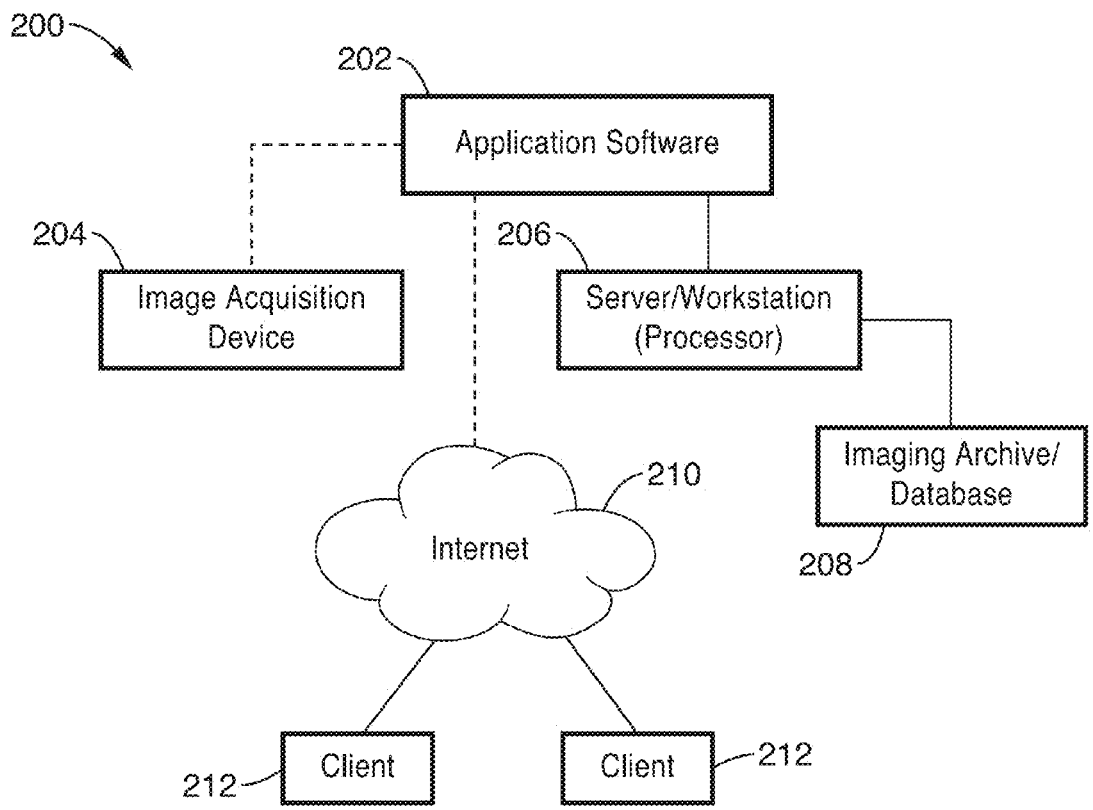
FIG. 8 is a schematic diagram of a lung, lobe and fissure image segmentation system of the present invention.

FIG. 8 shows a schematic diagram of system 10 wherein one or more steps or methods identified in FIG. 1 through FIG. 6 are implemented as computer application software 202. In one embodiment, application software 202 may be run on a processor such as an individual medical imaging workstation 206, e.g. either at the image acquisition device (CT scanner) 204, or on a reading workstation. The application software 202 may also be run on a centralized server 206 or cluster of servers in a radiology department or medical center. Running on a server 206 may offer some advantages in terms of interfacing with a centralized imaging archive and storing reports in a centralized database 208. The system 200 may also be accessed remotely (via the Internet 210), for example, using GRID computing. Using this approach, the system 200 is made available as a GRID service and clients 212 with proper authentication/authorization can access it world-wide.

Figure 7B:
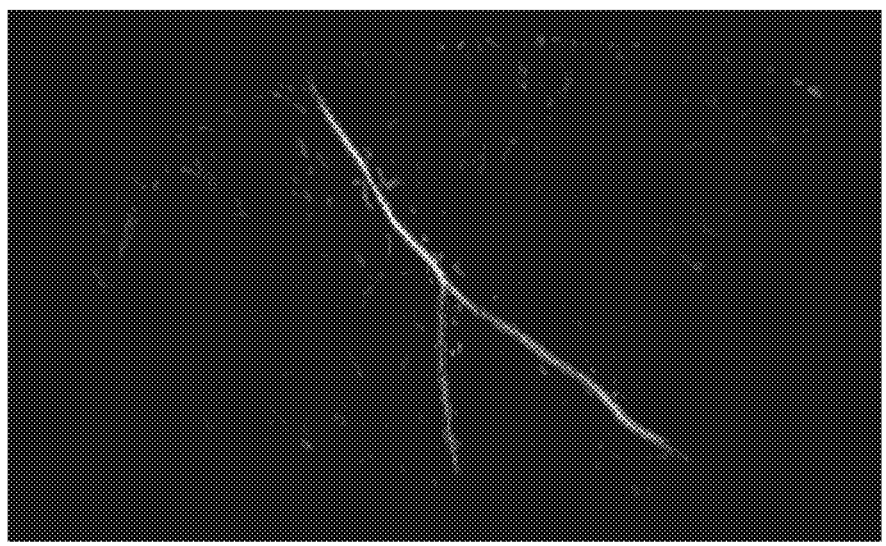
FIG. 7B shows an image of kNN classification of fissures using gradient analysis of the Hessian matrix.
Figure 7A:
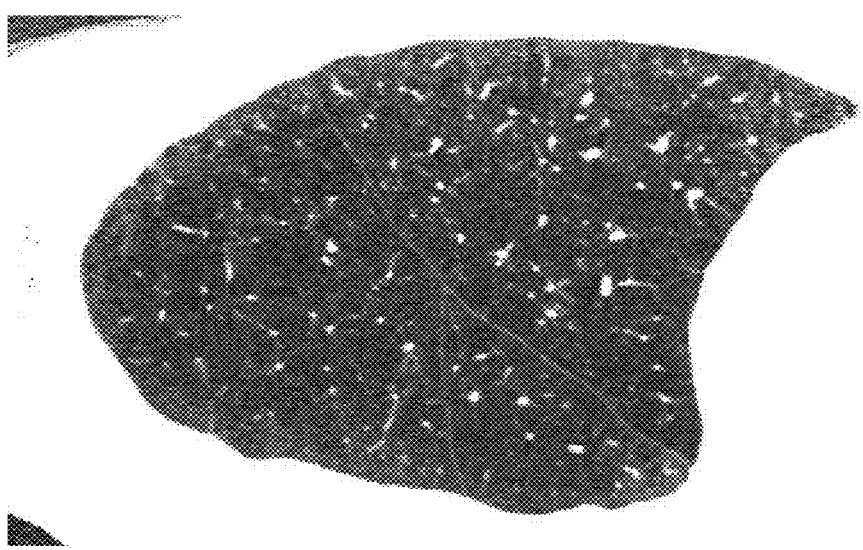
FIG. 7A shows a saggital CT image of the right lung.
Figure 7D:
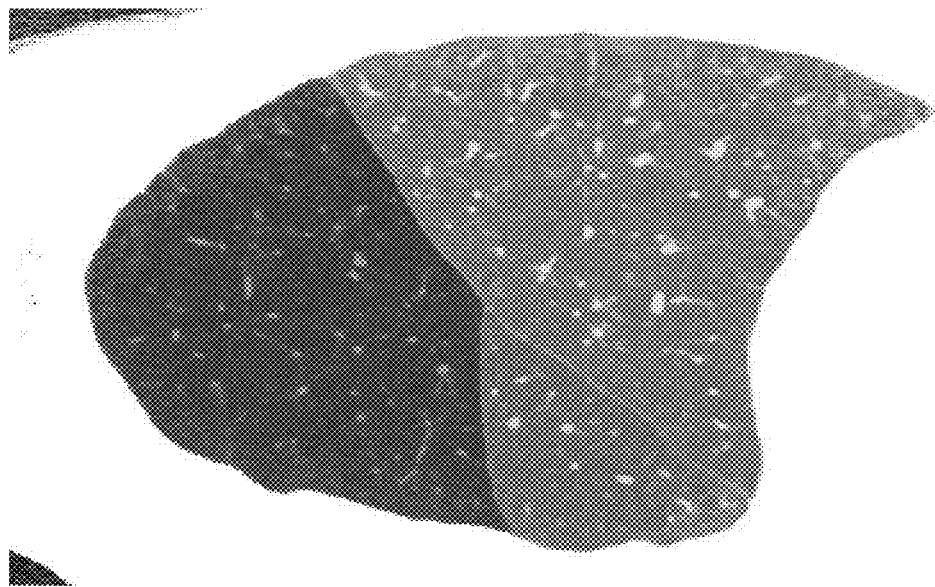
FIG. 7D is an image of the resulting lobar segmentation in accordance with the present invention.
Figure 7C:
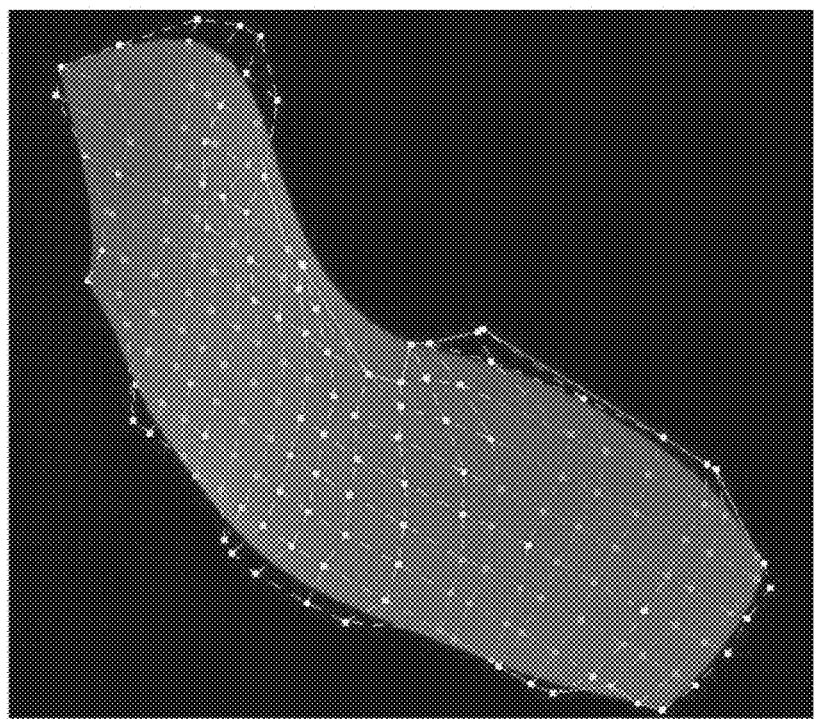
FIG. 7C is an image of a 3D surface construction of a fitted major fissure in accordance with the present invention.

FIG. 7A through FIG. 7D show actual graphic output according to the system 200 and method 10 of the present invention. FIG. 7A is an exemplary saggital CT image of the right lung. FIG. 7B shows an image of kNN classification of fissures using gradient analysis of the Hessian matrix according to method 10 of the present invention. FIG. 7C is an image of a 3D surface construction of a fitted major fissure in accordance with method 10 of the present invention. FIG. 7D is an image of the resulting lobar segmentation in accordance with method 10 the present invention.

Example Segmentation Methods

The following discussion details an iterative approach for the segmentation (e.g. segmentation module 30 in FIG. 1) of pulmonary lobes via a surface that evolves based on a voxel based fissure confidence function and a smooth prior. The method comprises two main components: 1) computation of the fissure confidence function and 2) the surface evolution algorithm.

a. Fissure Confidence Function

A supervised fissure enhancement filter based is used for the fissure confidence function. The filter comprises a two stage K nearest neighbor (KNN) classifier that are trained to distinguish between fissure and non-fissure voxels. In the first stage, a set of Gaussian derivative and Hessian based features are computed at different scales from the CT scans for all training samples, which belong to either the fissure class or non-fissure class. The computed features are then used to train the stage one KNN classifier, which estimates the probability of a voxel being a fissure as the fraction of samples that are fissures among the K nearest neighbors. In the second stage, Gaussian derivative and Hessian based features of the training samples are computed from the first stage probability image. The probability image based features are then combined with the CT scan based features computed in the first stage. The combined features are then used again to train a stage two KNN classifier, which results in the final probability estimates of a voxel being a fissure. Although the results of the supervised fissure enhancement filter are good, they may be noisy at times, e.g., misclassifying voxels adjacent to a fissure, resulting in a thick slab of detected fissure. In order to remove such noise and to better localize actual fissure voxels, the following confidence C function for a voxel x were defined as:

$$C(x) = \begin{cases} P(x; \sigma) + \left(1 - \left|\frac{\lambda_2(x; \sigma)}{\lambda_1(x; \sigma)}\right|\right), & \text{if } \lambda(x; \sigma) < 0 \\ 0, & \text{otherwise} \end{cases} \quad \text{Eq. 10}$$

where $P(\cdot; \sigma)$ is the probability of the enhanced image observed under a Gaussian kernel of scale $\sigma$, and $\lambda_1(x; \sigma) \geq \lambda_2(x; \sigma)$ are the largest and the second largest eigenvalues from the Hessian matrix computed at x under the scale $\sigma$ Intuitively, the confidence of a voxel will only have a non-zero value if its probability is higher than the voxels nearby. In order to have a high confidence, a voxel must have a high probability of belonging to the fissure and its surroundings resemble a plate like structure.

b. Surface Evolution Algorithm

Figure 9:
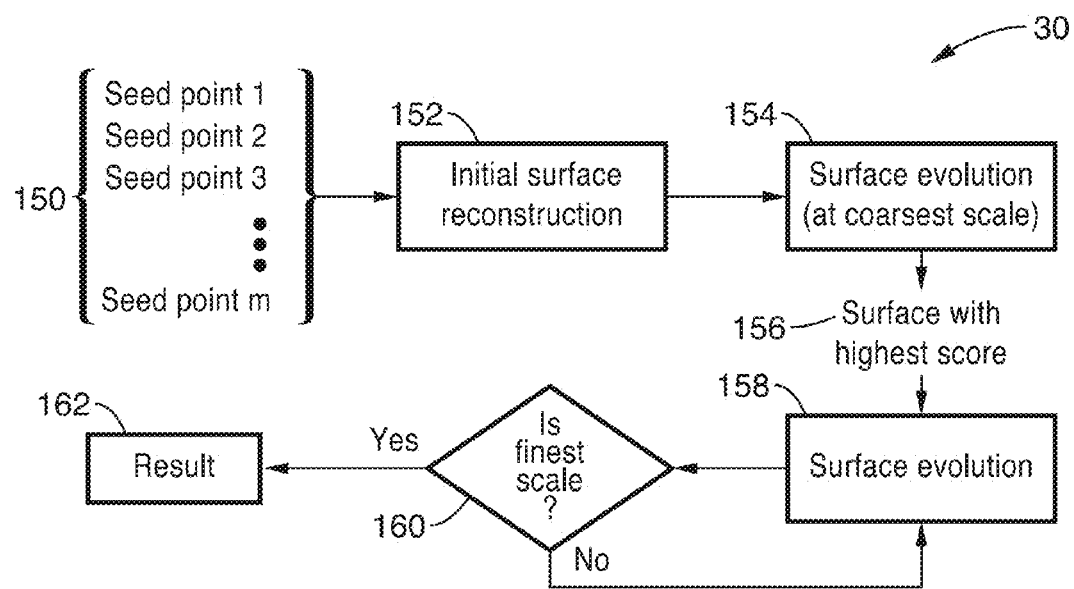
FIG. 9 is a schematic flow diagram of the surface evolution algorithm for segmentation in accordance with the present invention.

A surface in the form of a height map is represented that resides on a 2D reference plane, which has a normal n and passes through a point $x_0$. All points $p \in \mathbb{R}^2$ in the 2D reference plane contain the height of the surface in the normal direction from the reference plane, which can be mapped to a surface voxel coordinate via a function $\mathbb{R}^2 \rightarrow \mathbb{R}^3$. Referring to FIG. 9, the surface evolution algorithm (which is a component of segmentation module 30) starts with a number of seed points 150 that have the highest fissure confidence at the coarsest scale. At block 152, an initial surface is then constructed for each of the seed points. Subsequently at block 154, the initial surfaces are admitted into the evolution process at the coarsest scale, where the initial surfaces are evolved such that the total confidence of all points on the surface is maximized, with the constraint that the resulting surface must be smooth. Upon completion of the evolution process, the surface scores of the resulting surfaces are computed. The surface score is defined as the median of the confidence of all points on the final surface. The surface with the highest surface 156 score is then retained, where it will proceed to the evolution process at finer scales. At block 160, surface evolution from block 158 is compared against a threshold value, and repeats until the finest scale is reached. The whole process finishes at the finest scale 162.

Given a seed point, the 2D reference plane of the height map used for representing the surface is constructed by using the coordinate of the seed point and the eigenvector corresponding to $\lambda_1$ as $x_0$ and n respectively. Starting from $p_0$, which is the point on the height map that is corresponding to the seed point, and with an initial height of zero, a new height is obtained by searching within a neighborhood of 10 voxels for the nearest point that forms a maxima in terms of the confidence in Eq. 10. The newly obtained height is then stored and propagated to neighboring points in the height map. The same height searching and propagating process is then repeated for the neighboring points and so on. The initial surface is obtained once all points in the height map are processed.

During the evolution process at a particular scale $\sigma$, the surface is iteratively evolved such that the total confidence measure computed at $\sigma$ is maximized, with the constraint that the surface must be smooth. Each iteration in the evolution process contains three steps, which are displacement, smoothing and reconstruction. In the displacement step, the height of all the points in the height map are adjusted independently, such that the total confidence measure of all points is maximized. This is achieved by searching locally, within a radius of 10 voxels, for the nearest local maxima in the confidence. Once the new heights of all the points in the height map are determined, the smoothing step is performed by applying a modified Laplacian smoothing algorithm on the heights, where the update equation for the height of a point p in the height map is defined as:

$$h_{t+1}(p) = (1 - \omega(p))h(p) + \frac{\omega(p)}{|\Omega_p|} \sum_{q \in \Omega_p} h_t(q) \quad \text{Eq. 11}$$

where $\Omega p$ is a set containing the immediate four neighbors of p. The weight $\omega$ that controls the amount of smoothing occurred in each iteration of the modified Laplacian smoothing algorithm is designed such that less smoothing (lower weight) occur at points with high confidence compared to those with lower confidence, and is defined as:

$$\omega(p) = \min\left(\alpha_{max}\left(1 - \frac{C(f(p))}{\max(S)}\right), \alpha_{min}\right) \quad \text{Eq. 12}$$

where S is the set containing the confidence of all the points on the surface prior to smoothing, and $\omega_{min}$ and $\omega_{max}$ are the minimum and maximum possible smoothing weight respectively.

The final step is reconstruction to adjust the reference plane of the height map so that it is optimal for representation of the surface. By extracting the voxel coordinates of all points on the surface that have a non-zero fissure confidence, the mean coordinates and the covariance matrix of the extracted coordinates are computed. For the covariance matrix, the points are weighted according to their corresponding confidence. The $x_0$ of the new reference plane is then the mean coordinates, and n is the eigenvector corresponding to the smallest eigenvalue of the covariance matrix. Finally, the coordinates of the previously extracted points are mapped back to the height map constructed with the new reference plane. For those points on the height map that do not correspond to any of the extracted coordinates, their heights are interpolated via a linear tensioning scheme.

Given a segmented left lung and a surface obtained from the surface evolution algorithm, we can now separate the lung into the upper and lower lobe by first projecting all voxels in the lung region to the reference plane of the height map, resulting in a projected point and a projected height for each voxel. A voxel is defined as belonging to the upper lobe if its projected height is larger than the height of the corresponding projected point in the height map, or belonging to the lower lobe if otherwise.

For the right lung, the same process is first used to obtain an initial upper and lower lobe. Due to the lack of spatial priors, the surface that we initially obtain may be composed of both the major and minor fissure. Therefore it is possible that the middle lobe may be located in either the "upper" or "lower" lobe. In order to solve this problem, two surface evolution algorithms are initiated independently in the two initial lobes. The resulting surface with the highest surface score, computed at the finest scale, will then be used to separate its corresponding initial lobe to obtain the middle lobe. Finally, morphological opening using a sphere of two voxels radius is applied to the obtained middle lobe, where only the largest component of the middle lobe after opening is retained.

When extracting the second fissure from the right lung, in order to ensure that part of the second fissure overlaps with the first fissure, the confidence is modified to accommodate a fissure attracting force, as shown below:

$$C'(x) = \begin{cases} \max\left(C(x), \alpha \exp\left(\frac{dist(x)}{2\beta^2}\right)\right), & \text{if } C(x) > 0 \\ 0, & \text{otherwise} \end{cases} \quad \text{Eq. 13}$$

where dist(·) is a function that returns the shortest distance of a point to the first fissure, $\alpha$ and $\beta$ control the magnitude and spread of the fissure attracting force. In order to prevent the extraction of the second fissure from returning a fissure that completely overlaps with the first fissure, the stopping criterion is modified to only stop if the distance between the extracted second fissure and the first fissure is at least ten voxels apart. In the case where the distance between the second and first fissure is too near, the corresponding seed point will be discarded and the surface evolution algorithm will be repeated again.

c. Experiment 1

Training of the supervised fissure enhancement filter and tuning of the parameters for the method in sections A and B above was performed using a total of 18 chest CT scans obtained from a research database, with slice thickness and in-plane resolution ranging from 0.55 to 0.78 mm and from 0.5 to 1.25 mm respectively. The method was tested on chest CT scans from another research database, consisting of 41 scans from different patients with severe emphysema and forced expiratory volume in one second (FEV1)<45%. The slice thickness and in-plane resolution of the test set ranged from 0.5 to 1.0 mm and 0.54 to 0.83 mm respectively.

Approximate nearest neighbor searching was used to implement the KNN classifiers of the supervised fissure enhancement filter, where the number of nearest neighbor K was set to fifteen and an error bound $\epsilon$ of 0.5 was used. To reduce computational time, the multiple scales used for computing the confidence and performing the evolution process were implemented in the form of a Gaussian pyramid. The probability image from the supervised fissure enhancement filter was first filtered with a Gaussian kernel of $\sigma=1$ voxel, resulting in the image at scale level one. By filtering the image with the same Gaussian kernel and subsampling the resulting image at a factor of two, the image at the second scale level is obtained, where the same process is repeated to obtain images at higher scale level. A total of four scale levels were used in this work. The finite difference method was used to approximate Eq. 10 using the images from the Gaussian pyramid.

A total of 100 seed points were used in the surface evolution algorithm. In our implementation, a simple stopping criterion of stopping after N iterations was used for the evolution process. The value N was set to $50n_s$, where $n_s=1, 2, 3, 4$ indicates scale level in the evolution process, with $n_s=1$ being the finest scale. The number of smoothing iteration for the smoothing process was set to 100 for $n_s=4$, and was divided by two whenever $n_s$ is decreased (proceeding to finer scale). The minimum weight $\omega_{min}$ and maximum weight $\omega_{max}$ were set to 0.01 and 0.3 respectively. For the modified confidence in Eq. 13, the magnitude $\alpha$ and spread $\beta$ of the fissure attracting force were set to 0.1 and 3 respectively.

The lungs of the test scans were segmented. Overlap ratio was used as a performance measure. A slack border of 2 mm from manually drawn borders was introduced, where voxels within the slack border were not taken into account when computing the overlap ratio. The reason for the slack border was to allow for possible inaccuracy in the manual reference, as it is difficult at times to identify fissures exactly, especially in the case where fissures are incomplete.

For the left lung, the average overlap ratio of the upper lobe and lower lobe were 0.96 and 0.95 respectively, where the proposed method performed successfully on all cases, with the exception of a single case where the subject had a prominent accessory fissure that was incorrectly detected as the major fissure. For the right lung, the average overlap ratio was 0.91, 0.90 and 0.61 for the upper, lower and middle lobe, respectively. The relatively low overlap ratio of the right middle lobe is caused by seven cases, where nearly the entire minor fissure was not visible in the scan, and by six cases, where the initial lobe for computing the second fissure was wrongly selected. If the seven cases with nearly the whole of the minor fissure missing were excluded, and the wrongly selected initial lobes for the six cases were manually corrected, the average overlap ratio of the right middle lobe improves to 0.86.

Figure 10A:
FIG. 10A and FIG. 10B show segmentation results of the left lung and right lung, respectively, using the surface evolution algorithm of FIG. 9.
Figure 10B:

FIG. 10A and FIG. 10B show the results of the lobes extracted from both the right and left lungs. From left to right are the original image, manual reference and results from the method detailed in sections A and B above. The upper lobe, lower lobe and middle lobe are shaded separately.

Although not utilized in the proposed method, another embodiment would include incorporating fissure anatomical and spatial priors to further improve both performance and robustness of the method. One approach would be by including these priors as a term in the confidence function in Eq. 10. Another approach would be to use fissure priors to generate initial surfaces for the evolution process, e.g., from a generative model of the fissures, instead of reconstructing them from seed points as described above for FIG. 9.

d. Experiment 2

Training of the supervised fissure enhancement filter and tuning of the parameters for the method described above in sections a and b was performed using a total of 18 chest CT scans obtained from a research database, with slice thickness and in-plane resolution ranging from 0.50 to 1.25 mm and 0.55 to 0.78 mm respectively. The method was tested on chest CT scans from another research database, consisting of 22 scans from different patients with either idiopathic pulmonary fibrosis or severe emphysema (forced expiratory volume in one second <45%). The slice thickness and in-plane resolution of the test set ranged from 0.6 to 3.0 mm and 0.59 to 0.80 mm respectively.

Accordingly, the systems and methods of the present invention provide a powerful automation combined with intuitive, human intervention and feedback to achieve a robust, widely-applicable system that can even handle the most diseased or abnormal images where fully automated segmentation is not possible. The automated pre-processing of data performed by the method 10 of the present invention is of significant importance, since manual segmentation of large numbers of scans would be impractical.

As a preprocessing step, the lungs of all test scans were segmented. Approximate nearest neighbor searching was used to implement the KNN classifiers of the supervised fissure enhancement filter, where the number of nearest neighbor K was set to fifteen and an error bound $\epsilon$ of 0.5 was used. To reduce computational time, the multiple scales used for computing the confidence and performing the evolution process were implemented in the form of a Gaussian pyramid. The probability image from the supervised fissure enhancement filter was first filtered with a Gaussian kernel of $\sigma=1$ voxel, resulting in the image at scale level one. By filtering the image with the same Gaussian kernel and subsampling the resulting image at a factor of two, the image at the second scale level is obtained. The same process is repeated to obtain images at higher scale level. A total of four scale levels were used in this work. The finite difference method was used to approximate Eq. 10 using the images from the Gaussian pyramid.

To further reduce the computation time, the surface evolution algorithm was modified to stop at the second finest level instead of the finest level. A simple stopping criterion of stopping after N iterations was used for the evolution process. The value N was set to $10 n_s$, where $n_s=2, 3, 4$ indicates scale level in the evolution process, with $n_s=2$ being the second finest scale. The number of smoothing iteration for the smoothing process was set to 100 for $n_s=4$, and was divided by two whenever $n_s$ is decreased (proceeding to finer scale). The minimum weight $\omega_{min}$ and maximum weight $\omega_{max}$ were set to 0.01 and 0.3 respectively.

Semi-automated segmentation of the lobes using the method of sections a. and b. above were performed. Initialization from scratch was used when a fissure detected from the automated segmentation were too different from the truth. User input points required by the proposed method were provided by drawing lines on either the axial, coronal or sagittal viewing plane.

Figure 11A:
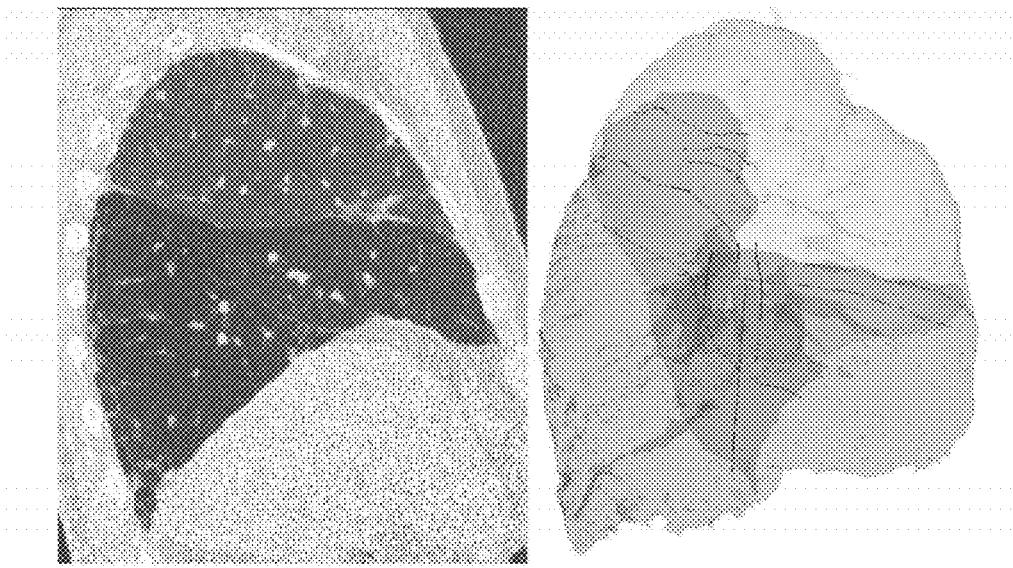
FIG. 11A and FIG. 11B show an original CT scan overlaid with segmentation results of the left lung and right lung, respectively, using the surface evolution algorithm of FIG. 9.
Figure 11B:
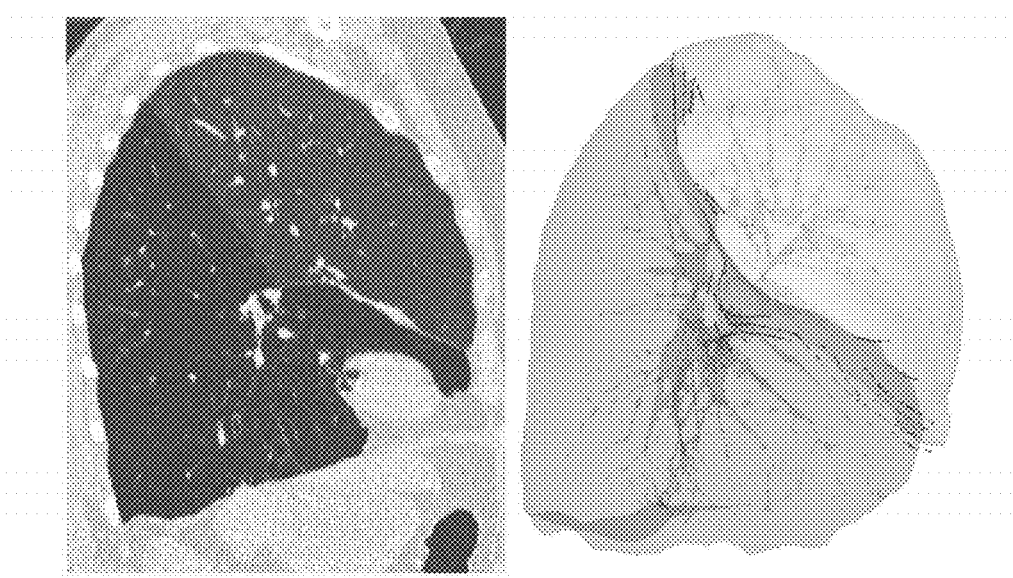

Table 1 shows the number of interactions required for the test cases, measured in the number of line segments drawn. Excluding the computation time of the supervised enhancement filter, segmenting the lobes interactively for a test case takes on average 20 minutes (including loading and processing), depending on how easy it is to locate the fissures visually. FIG. 11A and FIG. 11B show surface rendering of the segmented lobes and the line segments provided for the fissures in a left and a right lung.

In one alternative embodiment, the method may include pre-computing the fissure confidence instead of computing it on the fly. Also, the loading and preprocessing time for each fissure before the user can start editing may be alleviated by taking advantage of multi-threading technology by moving certain processing into background to remove such wait time and thus further shorten user interaction time.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. A method for automatically segmenting an image of a patient's lung, comprising: inputting data from one or more computed tomography images; segmenting a thoracic airspace by intensity-thresholding image voxels; subdividing the thoracic airspace into axial 2D components; identifying a midline of the airspace; detecting a maximum intensity cost path in a region associated with the midline; and assigning 2D components to left and right regions of interest based on the detected maximum intensity cost path.

2. A method as recited in any of the previous embodiments, further comprising: generating a fissure probability image from the left and right region of interest data.

3. A method as recited in any of the previous embodiments, wherein generating a fissure probability image comprises: computing a set of Gaussian derivative and Hessian-based features for each voxel identified in the left and right regions of interest; and inputting the features to a binary KNN classifier.

4. A method as recited in any of the previous embodiments, further comprising: generating a fissure surface mesh from the fissure probability image.

5. A method as recited in any of the previous embodiments, wherein generating a fissure surface mesh comprises: calculating a 3D surface of the image data as a height map from a 2D reference plane.

6. A method as recited in any of the previous embodiments, wherein generating a fissure surface mesh comprises: generating a fissure confidence image from the fissure probability image.

7. A method as recited in any of the previous embodiments, wherein the fissure confidence image is a function of eigenvalues and eigenvectors of a Hessian matrix associated with the image data.

8. A method as recited in any of the previous embodiments, wherein plateness features are calculated to generate the fissure confidence image.

9. A method as recited in any of the previous embodiments, wherein a height map is generated by identifying seed points having a highest confidence value.

10. A method as recited in any of the previous embodiments, further comprising: segmenting the left and right regions of interest to form a plurality of segmented lung lobes.

11. A method as recited in any of the previous embodiments, wherein the segmented lung lobes comprise: a left lower lung lobe, left upper lung lobe, right upper lung lobe, right middle lung lobe, and right lower lung lobe.

12. A method as recited in any of the previous embodiments further comprising: allowing user modification of one or more of the fissure probability image and fissure surface mesh; and re-segmenting the left and right regions of interest to generate the segmented lung lobes.

13. A method as recited in any of the previous embodiments, further comprising: generating volume and density measurements from the segmented lung lobes.

14. A method as recited in any of the previous embodiments, further comprising: generating fissure integrity scores from one or more of the fissure probability image and fissure surface mesh.

15. A system for automatically segmenting in image of a patient's lung, comprising: a processor; software executable on the processor for; inputting data from one or more computed tomography (CT) images; segmenting a thoracic airspace by intensity-thresholding image voxels; subdividing the thoracic airspace into axial 2D components; identifying a midline of the airspace; detecting a maximum intensity cost path in a region associated with the midline; and assigning 2D components to left and right regions of interest based on the detected maximum intensity cost path.

16. A system as recited in any of the previous embodiments, the software further executable on the processor for: generating a fissure probability image from the left and right region of interest data.

17. A system as recited in any of the previous embodiments, wherein generating a fissure probability image comprises: computing a set of Gaussian derivative and Hessian-based features for each voxel identified in the left and right regions of interest; and inputting the features to a binary KNN classifier.

18. A system as recited in any of the previous embodiments, the software further executable on the processor for: generating a fissure surface mesh from the fissure probability image.

19. A system as recited in any of the previous embodiments, wherein generating a fissure surface mesh comprises: calculating a 3D surface of the image data as a height map from a 2D reference plane.

20. A system as recited in any of the previous embodiments, wherein generating a fissure surface mesh comprises: generating a fissure confidence image from the fissure probability image.

21. A system as recited in any of the previous embodiments, wherein the fissure confidence image is a function of eigenvalues and eigenvectors of a Hessian matrix associated with the image data.

22. A system as recited in any of the previous embodiments, wherein plateness features are calculated to generate the fissure confidence image.

23. A system as recited in any of the previous embodiments, wherein a height map is generated by identifying seed points having a highest confidence value.

24. A system as recited in any of the previous embodiments, further comprising: segmenting the left and right regions of interest to form a plurality of segmented lung lobes.

25. A system as recited in any of the previous embodiments, wherein the segmented lung lobes comprise: a left lower lung lobe, left upper lung lobe, right upper lung lobe, right middle lung lobe, and right lower lung lobe.

26. A system as recited in any of the previous embodiments, further comprising: allowing user modification of one or more of the fissure probability image and fissure surface mesh; and re-segmenting the left and right regions of interest to generate the segmented lung lobes.

27. A system as recited in any of the previous embodiments, further comprising: generating volume and density measurements from the segmented lung lobes.

28. A system as recited in any of the previous embodiments, further comprising: generating fissure integrity scores from one or more of the fissure probability image and fissure surface mesh.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

The number of line segments drawn by the user

|  | Left major fissure | Right major fissure | Right minor fissure | All fissures |
|---|---|---|---|---|
| Average | 13.5 | 13.7 | 9.5 | 36.8 |
| Standard Dev | 5.0 | 4.8 | 4.1 | 7.8 |
| Min | 3 | 5 | 3 | 18 |
| Max | 20 | 25 | 19 | 47 |

What is claimed is:
1. A method for automatically segmenting an image of a patient's lung, comprising:
    inputting data from one or more computed tomography images;
    segmenting a thoracic airspace by intensity-thresholding image voxels;

subdividing the thoracic airspace into axial 2D components;
identifying a midline of the airspace;
detecting a maximum intensity cost path in a region associated with the midline; and
assigning 2D components to left and right regions of interest based on the detected maximum intensity cost path.

2. A method as recited in claim 1, further comprising:
generating a fissure probability image from the left and right region of interest data.

3. A method as recited in claim 2, wherein generating a fissure probability image comprises:
computing a set of Gaussian derivative and Hessian-based features for each voxel identified in the left and right regions of interest; and
inputting the features to a binary KNN classifier.

4. A method as recited in claim 2, further comprising:
generating a fissure surface mesh from the fissure probability image.

5. A method as recited in claim 4, wherein generating a fissure surface mesh comprises:
calculating a 3D surface of the image data as a height map from a 2D reference plane.

6. A method as recited in claim 4, wherein generating a fissure surface mesh comprises:
generating a fissure confidence image from the fissure probability image.

7. A method as recited in claim 6, wherein the fissure confidence image is a function of eigenvalues and eigenvectors of a Hessian matrix associated with the image data.

8. A method as recited in claim 6, wherein plateness features are calculated to generate the fissure confidence image.

9. A method as recited in claim 6, wherein a height map is generated by identifying seed points having a highest confidence value.

10. A method as recited in claim 6, further comprising:
generating fissure integrity scores from one or more of the fissure probability image and fissure surface mesh.

11. A method as recited in claim 4, further comprising:
segmenting the left and right regions of interest to form a plurality of segmented lung lobes.

12. A method as recited in claim 11, wherein the segmented lung lobes comprise: a left lower lung lobe, left upper lung lobe, right upper lung lobe, right middle lung lobe, and right lower lung lobe.

13. A method as recited in claim 11, further comprising:
allowing user modification of one or more of the fissure probability image and fissure surface mesh; and
re-segmenting the left and right regions of interest to generate the segmented lung lobes.

14. A method as recited in claim 11, further comprising:
generating volume and density measurements from the segmented lung lobes.

15. A system for automatically segmenting an image of a patient's lung, comprising:
a processor;
software executable on the processor for;
inputting data from one or more computed tomography (CT) images;
segmenting a thoracic airspace by intensity-thresholding image voxels;
subdividing the thoracic airspace into axial 2D components;
identifying a midline of the airspace;
detecting a maximum intensity cost path in a region associated with the midline; and
assigning 2D components to left and right regions of interest based on the detected maximum intensity cost path.

16. A system as recited in claim 15, the software further executable on the processor for:
generating a fissure probability image from the left and right region of interest data.

17. A system as recited in claim 16, wherein generating a fissure probability image comprises:
computing a set of Gaussian derivative and Hessian-based features for each voxel identified in the left and right regions of interest; and
inputting the features to a binary KNN classifier.

18. A system as recited in claim 16, the software further executable on the processor for:
generating a fissure surface mesh from the fissure probability image.

19. A system as recited in claim 18, wherein generating a fissure surface mesh comprises:
calculating a 3D surface of the image data as a height map from a 2D reference plane.

20. A system as recited in claim 18, wherein generating a fissure surface mesh comprises:
generating a fissure confidence image from the fissure probability image.

21. A system as recited in claim 20, wherein the fissure confidence image is a function of eigenvalues and eigenvectors of a Hessian matrix associated with the image data.

22. A system as recited in claim 20, wherein plateness features are calculated to generate the fissure confidence image.

23. A system as recited in claim 20, wherein a height map is generated by identifying seed points having a highest confidence value.

24. A system as recited in claim 20, further comprising:
generating fissure integrity scores from one or more of the fissure probability image and fissure surface mesh.

25. A system as recited in claim 18, further comprising:
segmenting the left and right regions of interest to form a plurality of segmented lung lobes.

26. A system as recited in claim 25, wherein the segmented lung lobes comprise: a left lower lung lobe, left upper lung lobe, right upper lung lobe, right middle lung lobe, and right lower lung lobe.

27. A system as recited in claim 25, further comprising:
allowing user modification of one or more of the fissure probability image and fissure surface mesh; and
re-segmenting the left and right regions of interest to generate the segmented lung lobes.

28. A system as recited in claim 25, further comprising:
generating volume and density measurements from the segmented lung lobes.

* * * * *